(12) United States Patent
Bauer et al.

(10) Patent No.: US 7,986,410 B2
(45) Date of Patent: *Jul. 26, 2011

(54) METHOD FOR DETECTING A FIBROUS WEB TEAR IN A DRYING SECTION OF A MACHINE FOR PRODUCING THE FIBROUS WEB AND APPARATUS FOR PERFORMING SAID METHOD

(75) Inventors: Armin Bauer, St. Pölten (AT); Dietmar Üblacker, Neuhofen (DE)

(73) Assignee: Voith Patent GmbH, Heidenheim (DE)

( * ) Notice: Subject to any disclaimer, the term of this patent is extended or adjusted under 35 U.S.C. 154(b) by 302 days.

This patent is subject to a terminal disclaimer.

(21) Appl. No.: 12/050,621

(22) Filed: Mar. 18, 2008

(65) Prior Publication Data

US 2009/0237664 A1   Sep. 24, 2009

(51) Int. Cl.
*G01N 21/84*   (2006.01)

(52) U.S. Cl. .............. 356/430; 356/238.1; 356/429

(58) Field of Classification Search .......... 356/429–431, 356/238.1–238.3; 702/40, 170, 172; 162/198, 162/263, 255; 83/371, 360, 177
See application file for complete search history.

(56) References Cited

U.S. PATENT DOCUMENTS

| | | | |
|---|---|---|---|
| 3,552,252 A * | 1/1971 | Maxey et al. | 83/362 |
| 4,071,899 A * | 1/1978 | Holy | 250/559.44 |
| 4,837,715 A * | 6/1989 | Ungpiyakul et al. | 702/82 |
| 5,150,175 A * | 9/1992 | Whitman et al. | 356/429 |
| 5,590,577 A * | 1/1997 | Ruf et al. | 83/371 |
| 6,332,587 B1 * | 12/2001 | Moller et al. | 242/532.2 |
| 6,526,369 B1 * | 2/2003 | Meinecke et al. | 702/170 |
| 2008/0121362 A1 * | 5/2008 | Bauer et al. | 162/198 |

FOREIGN PATENT DOCUMENTS

| | | |
|---|---|---|
| DE | 91 01 972.9 U1 | 6/1991 |
| DE | 42 16 653 | 11/1993 |
| DE | 198 25 368 A1 | 9/1999 |

* cited by examiner

*Primary Examiner* — Sang Nguyen
(74) *Attorney, Agent, or Firm* — Taylor IP, PC

(57) ABSTRACT

This invention relates to a method for detecting a tear in a fibrous web in a drying section of a machine for producing the fibrous web, whereby the fibrous web is passed through the drying section by way of at least one dryer fabric, whereby the tear is detected by at least one optical web tear detection device, which includes at least one luminous source and one detector, and whereby a cut-off apparatus for the fibrous web is directly or indirectly activated by the web tear detection device. The optical web tear detection device is operated over an extended wave length range in order to detect a tear in the fibrous web reliably. In addition, the invention relates to an apparatus for performing the inventive method.

14 Claims, 2 Drawing Sheets

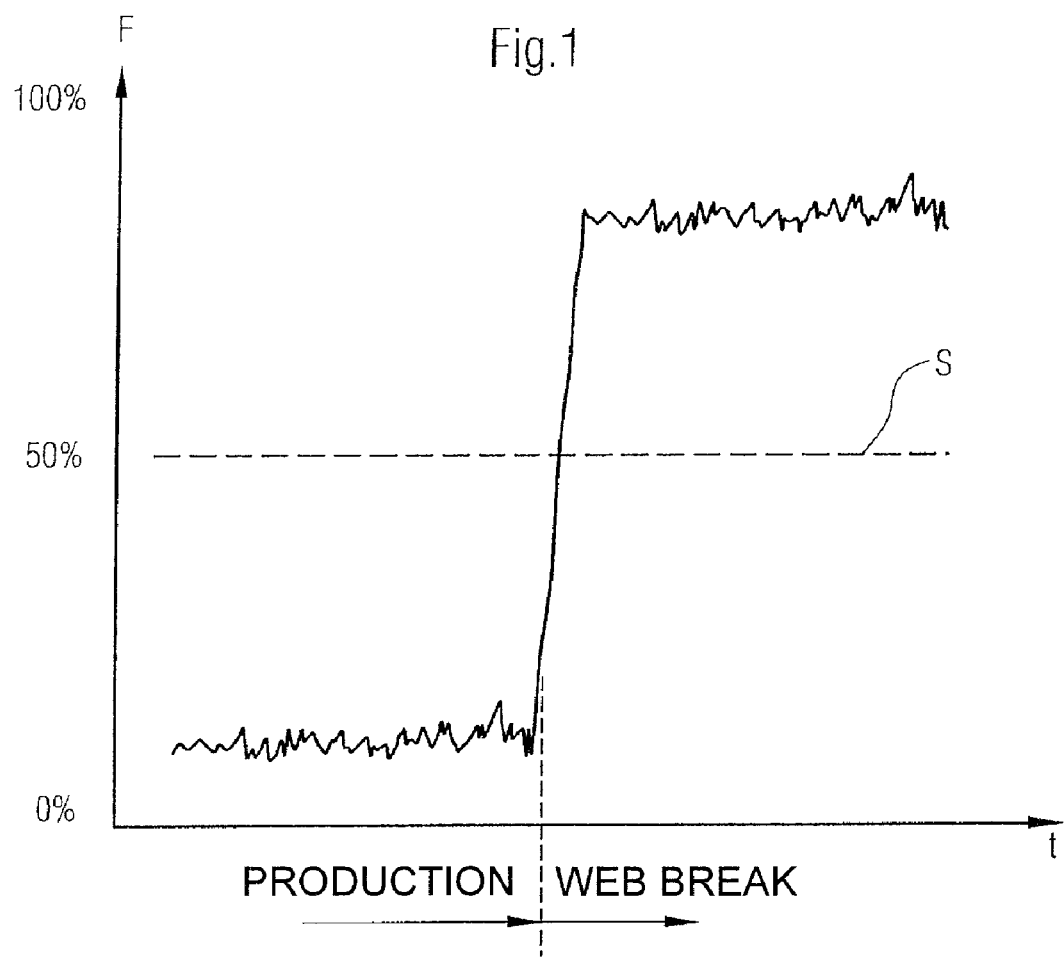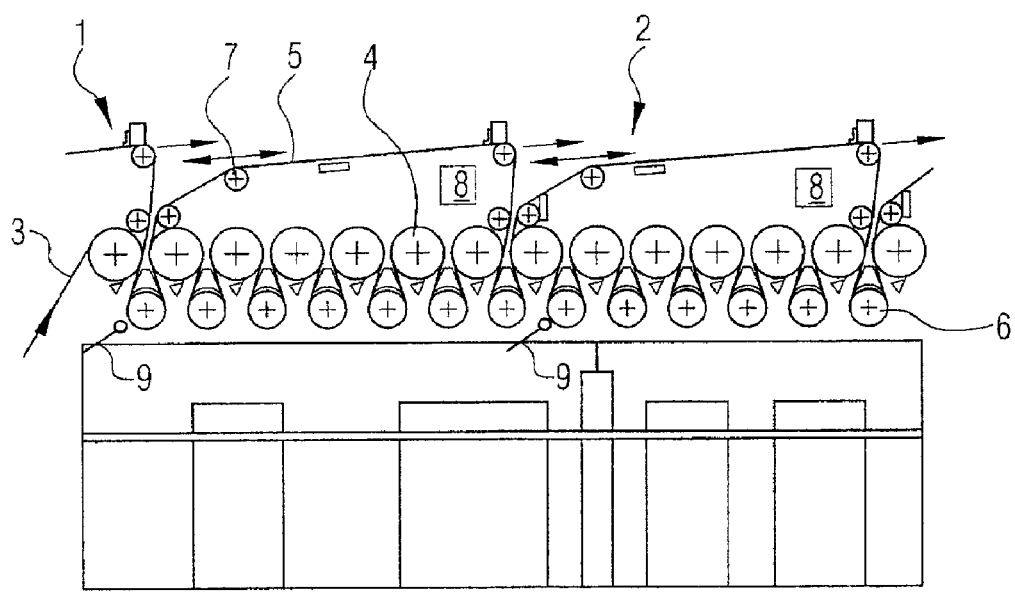

METHOD FOR DETECTING A FIBROUS WEB TEAR IN A DRYING SECTION OF A MACHINE FOR PRODUCING THE FIBROUS WEB AND APPARATUS FOR PERFORMING SAID METHOD

BACKGROUND OF THE INVENTION

1. Field of the Invention

This invention relates to a method for detecting a fibrous web tear in a drying section of a machine for producing the fibrous web, whereby the fibrous web is passed through the drying section by way of at least one dryer fabric, whereby the tear is detected by at least one optical web tear detection device which has a luminous source and a detector, and whereby a cut-off apparatus for the fibrous web is directly or indirectly activated by the web tear detection device.

In addition the invention relates to an apparatus for detecting a fibrous web tear in a drying section of a machine for producing the fibrous web, which is passed through the drying section by way of at least one dryer fabric, having at least one optical web tear detection device including a luminous source and a detector, and a cut-off apparatus for the fibrous web which is directly or indirectly activatable by the web tear detection device.

2. Description of the Related Art

During the production of all paper grades formed essentially from fibrous suspensions, the fast and reliable detection of tears in the fibrous web during its production is extremely important in order to prevent damage to parts of the machine used to produce the fibrous web.

At points at which the fibrous web is in free draw, web tears can be detected very reliably, for example by light barriers.

However, light barriers are unsuitable in situations in which the fibrous web rests on a skin acting as a web carrier, for example on a forming mesh, a press felt or a dryer fabric. Here use is made usually of optical systems on which a detector and a light or radiation source of the web tear detection device are mounted on the same side of the fibrous web.

Different web tear detection methods are known in this case.

For example, with the known "color detection" method, the difference in color between the fibrous web and the dryer fabric is used to detect the web tear. By way of example, FIG. 1 shows the signal flow, plotted in a color intensity/time diagram (F-t diagram), of an optical web tear detection device upon occurrence of a web tear. Upon overshooting or undershooting of a preselected trigger threshold value S (dashed line) of the color intensity F, a signal is sent to a cut-off apparatus. The trigger threshold value S for the signal to the cut-off apparatus can lie at for example 50% of the color intensity F. This method works particularly well with a distinct color difference such as that between a white fibrous web and a green dryer fabric for example.

A drawback of the color detection system is that it becomes more and more unreliable as the color difference between the fibrous web and the dryer fabric decreases. This is the case for example on machines for producing paperboard or packing paper, where brownish paper or paperboard webs lie on red or amber dryer fabrics. Here it is no longer possible to differentiate clearly between the fibrous web and the dryer fabric. This results in either web tear detection without a tear or in a tear without web tear detection. The former leads to an unnecessary stoppage of production and hence to financial loss for the plant operator, the latter runs the risk of causing damage to the machine.

Furthermore, dryer fabrics can become severely soiled the longer they are used, as the result of which the actual color of the dryer fabric is covered by dirt deposits. In such cases also it has been discovered that a color detection system no longer works reliably.

Another known method is the "detection of changes to light scatter (pseudo-structure detection)", whereby light is scattered differently on the structured dryer fabric than on the fibrous web. This difference is used to detect web tears. The measurement takes place at wave lengths a little above the visible range (800 to 1,000 nm).

It has been discovered that pseudo-structure detection systems likewise do not work reliably. This is owed presumably to soiling in the dryer fabric or to the transparency of the still partly wet fibrous web.

Furthermore, the two methods mentioned are designed for narrow-band detection, meaning that measurements are taken within a wave length range of only a few nanometers, from approximately 20 to 100. Some sensor models permit the intensities of different wave length ranges to be combined to form one summation signal, such as happens for example in the addition of the three intensity channels of an RGB sensor. Here too the spectrum is not continuously detected however.

Narrow-band detection often results in only a small signal difference between the reflected intensities of the dryer fabric and the fibrous web being obtained. As previously explained, this is the case for example on machines for producing paperboard or packing paper, where brownish paper or paperboard webs lie on red or amber dryer fabrics. This can result in either web tear detection without a tear or in a tear without web tear detection. The former leads to an unnecessary stoppage of production and hence to financial loss for the plant operator, the latter runs the risk of causing damage to the machine.

Another disadvantage of narrow-band detection is that both the luminous source and the detector of the web tear detection device have to be moved very close to the measuring point, for example to within 10 to 15 cm, in order to obtain a reasonable signal level. As the result, the device could be damaged by the fibrous web disengaging from the web guide in the event of a tear.

In addition, the detector is subject over the long term to various influences: the color tone of the dryer fabric changes, dirt deposits form on the dryer fabric, and the moisture content of the fibrous web on the measuring point is not always constant. This can be held in check to a certain degree through regular readjustment of the detector. For this purpose the reference signals and the trigger threshold value can be reset, and the detection wave length range can also be adapted.

From the German publication DE 42 16 653 A1 there is known for example a method for detecting web tears, with which the change of color tone of the dryer fabric is corrected by automatic re-referencing.

What is needed in the art is a method and an apparatus of the types initially referred to such that a more reliable detection of web tears compared to the prior art is made possible in particular in single-row drying sections of a machine for producing a fibrous web.

SUMMARY OF THE INVENTION

The present invention provides a method of the type initially referred to in that the optical web tear detection device is moved over an extended wave length range in order to detect a fibrous web tear reliably.

The inventive method has the great advantage of obtaining a larger signal difference between the fibrous web and the dryer fabric as compared to the methods initially referred to.

As the result, web tears can be far better detected. In addition it is possible to increase the measuring distance from the fibrous web and hence to move the optical web tear detection device further away from the danger area. Also, the detection wave length range no longer has to be adapted in the course of using the machine.

The optical web tear detection device is operated in a preferred embodiment in a wave length range from 200 to 1,100 nm, preferably from 400 to 800 nm or from 800 to 1,100 nm.

In the interest of a practical and sound embodiment, provision is made for the luminous source, such as in particular a halogen lamp, to emit preferably wide-band light. Such a luminous source has already proved to be highly successful in related fields and similar applications.

So that the inventive method can be used in as many applications as possible, including different applications if required, at least one filter can be installed between the luminous source and the detector of the optical device. The use of at least one filter permits major measurement modifications in return for only minor conversion measures and related costs.

Using the filter, the wave length range is set or limited preferably from 200 to 1,100 nm, preferably from 400 to 800 nm or from 800 to 1,100 nm. Using several filters, it is easily possible to limit the measured wave length range in upward and downward direction within the desired wave lengths.

In an embodiment of the present invention the detector measures in a wave length range from 200 to 1,100 nm, preferably from 400 to 800 nm or from 800 to 1,100 nm, because the wave lengths of the main components of the fibrous web such as lignin and/or cellulose are detected by the instruments in this case.

In addition, the wave length range for the measurement can also be limited by the detector and/or by the filter. This permits great flexibility in the use of the method in return for little technical outlay and manageable costs.

At least one preferably adjustable trigger threshold value can be set for the direct or indirect activation of the cut-off apparatus for the fibrous web by the web tear detection device. Hence the "activation behavior" of the cut-off apparatus can be selectively set dependent on the properties of the fibrous web.

The present invention thus provides an apparatus of the type initially referred to such that the optical web tear detection device can be moved over an extended wave length range in order to detect a fibrous web tear reliably.

The previously mentioned advantages of the invention are thus obtained.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 shows an exemplary signal flow of an optical web tear detection device upon occurrence of a web tear;

FIG. 2 shows a schematic representation of a subsection of a machine for producing a fibrous web according to an embodiment of the invention;

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 3:
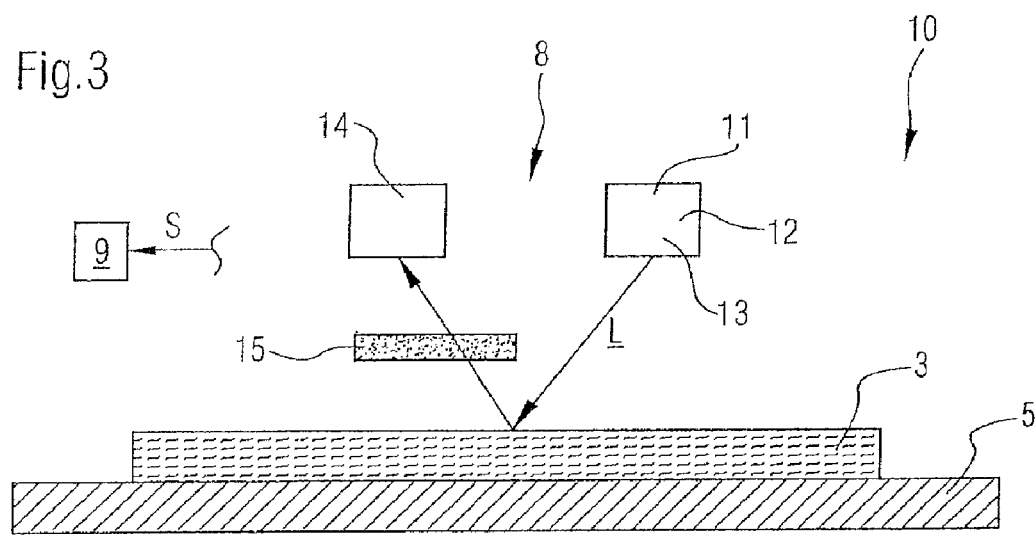
FIG. 3 shows a schematic representation of an arrangement of an inventive apparatus with an optical web tear detection device.

Referring now to the drawings, and more particularly to FIG. 2, there is shown schematically a side view of a detail of a drying section 2 of a machine, generally designated by 1, for producing a fibrous web 3.

Within the machine 1, the drying section 2 performs in known manner the function of removing moisture from a produced and/or processed fibrous web 3, meaning the function of drying it.

This is done in the example shown in FIG. 2 by way of contact drying, whereby a fibrous web 3 fed from the left in the drawing is dried by direct contact with a plurality of drying cylinders 4 on the one hand and an endless dryer fabric 5 circulating around the drying cylinders 4 on the other hand.

Presented in FIG. 2 are two dryer fabrics 5 in their complete path of rotation, whereby each of the dryer fabrics 5 circulates respectively around one group of drying cylinders 4. To be more precise, each dryer fabric 5 undulates in the region of the drying cylinders 4, whereby at the wave peak the dryer fabric 5 is deflected by a drying cylinder 4 and at the wave valley by a suction roller of a respective vacuum device 6. After leaving the last drying cylinder 4 of the respective group, the dryer fabric 5 is returned again via several guide rollers 7 to the first drying cylinder 4 of the group.

To perform the inventive method for detecting a tear in a fibrous web 3 in the drying section 2 of the machine 1 for producing the fibrous web 3, provision is made for each group of drying cylinders 4 to have at least one optical web tear detection device 8 (symbolically represented) which is described in principle later. Furthermore, provision is made for each group of drying cylinders 4 to have at least one cut-off apparatus 9 (only schematically represented) for the fibrous web 3, which is directly or indirectly activated by the optical web tear detection device 8.

FIG. 3 shows a schematic representation of an arrangement of an inventive apparatus 10 with an optical web tear detection device 8.

The apparatus 10 with the optical web tear detection device 8 can be used in particular in a drying section of a machine for producing a fibrous web 3. The fibrous web 3 rests in this case on the dryer fabric 5 which is transported through the drying section.

The optical web tear detection device 8 includes a wide-band luminous source 11 in the embodiment of a light source 12 such as a halogen lamp 13 or the like, and a detector 14, and said device can be operated in a wave length range L from 200 to 1,100 nm, preferably from 400 to 800 nm or from 800 to 1,100 nm, in order to detect a tear in the fibrous web 3 reliably. The luminous source 11 emits light in the mentioned wave length range L, said light being reflected by the fibrous web 3. The reflected light is then measured by the detector 14 and the signal received is evaluated in known manner. The settings, in particular the angles and the distances, as well as the luminous source 11 and the detector 14 can be selected in this case within a framework known to those skilled in the art.

In the embodiment shown, a filter 15 is installed between the luminous source 11 and the detector 14 of the optical web tear detection device 8, such as in the manner shown between the fibrous web 3 and the detector 14. In this case provision is made for the detector 14 to measure in a wave length range L from 200 to 1,100 nm, preferably from 400 to 800 nm or from 800 to 1,100 nm, and/or for the filter 15 to set the wave length range L from 200 to 1,100 nm, preferably from 400 to 800 nm or from 800 to 1,100 nm. The wave length range L for the measurement can thus be limited by the detector 14 and/or by the filter 15.

At least one trigger threshold value S is set for the direct or indirect activation of the cut-off apparatus 9 (only implied) for the fibrous web 3 by the web tear detection device 8.

The apparatus 10 shown in FIG. 3 with the optical web tear detection device 8 is also excellently suited in particular for performing the inventive method.

Figure 4:
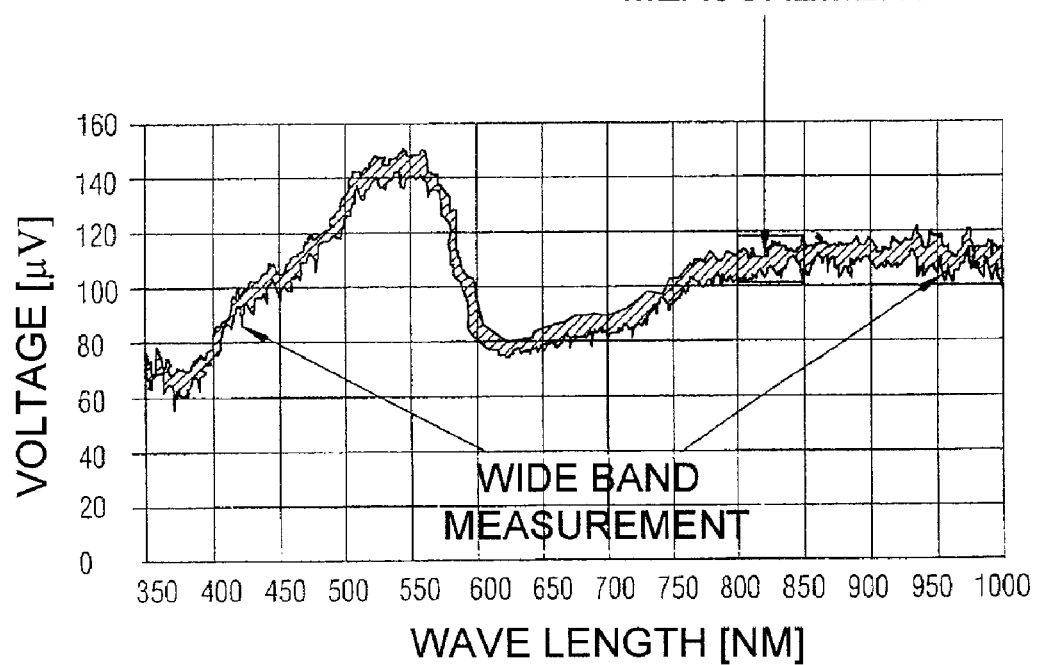
FIG. 4 shows a schematic representation of the wide-band method.

Finally, FIG. 4 shows a schematic representation of the wide-band method.

If two similar signals are compared over a narrow band range, represented by a small area, the outcome due to the small signal difference will be a poor signal-to-noise ratio and hence a poor possibility of differentiating between the signals. With a broad-band measurement, the integral of the signal difference over the measurement wave length range is far more pronounced, as the result of which the differentiability of the signals is greatly improved.

In summary it is to be recorded that the present invention develops further a method and an apparatus of the type initially referred to such that a more reliable detection of web tears compared to the prior art is made possible in particular in single-row drying sections of a machine for producing a fibrous web.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

LIST OF REFERENCE NUMERALS

1 Machine for producing a fibrous web
2 Drying section
3 Fibrous web
4 Drying cylinder
5 Dryer fabric
6 Vacuum device
7 Guide roller
8 Web tear detection device
9 Cut-off apparatus
10 Apparatus
11 Luminous source
12 Light source
13 Halogen lamp
14 Detector
15 Filter
F Color intensity
L Wave length range
S Trigger threshold value
t Time

What is claimed is:

1. A method for detecting a tear in a web of fibrous material in a drying section of a machine for producing the web, the web being passed through the drying section using at least one dryer fabric, said method comprising the steps of:
    detecting the tear by at least one optical web tear detection device, which includes at least one luminous source and one detector;
    operating said at least one optical web tear detection device over an extended wave length range to detect the tear in the web reliably, said at least one optical web tear detection device being operated in a full wave length range which is from 200 to 1,100 nm;
    measuring, with said detector and in said full wave length range, a reflected light; and
    activating, one of directly and indirectly, a cut-off apparatus for the web by said at least one optical web tear detection device dependent on said step of measuring with said detector in said full wave length range.

2. The method according to claim 1, wherein said at least one luminous source emits broad-band light.

3. The method according to claim 1, wherein said at least one luminous source is a halogen lamp.

4. The method according to claim 1, further including installing at least one filter between said at least one luminous source and said detector of said at least one optical web tear detection device.

5. The method according to claim 4, wherein, using said filter, said wave length range is one of set and limited from 200 to 1,100 nm.

6. The method according to claim 4, wherein said wave length range for said measuring step being limited by at least one of said detector and said filter.

7. The method according to claim 1, wherein at least one trigger threshold value is set for said step of activating, one of directly and indirectly, said cut-off apparatus for the web by said at least one optical web tear detection device.

8. An apparatus for detecting a tear in a web of fibrous material in a drying section of a machine for producing the web, which is passed through the drying section using at least one dryer fabric, said apparatus comprising:
    at least one optical web tear detection device including at least one luminous source and one detector, said at least one optical web tear detection device configured for being operated over an extended wave length range to detect the tear in the web reliably, said at least one optical web tear detection device being configured for being operated in a full wave length range which is from 200 to 1,100 nm, said detector configured for measuring, in said full wave length range, a reflected light; and
    a cut-off apparatus for the web, said cut-off apparatus configured for being one of directly and indirectly activated by said at least one optical web tear detection device dependent on said detector measuring, in said full wave length range, said reflected light.

9. The apparatus according to claim 8, wherein said at least one luminous source is a broad-band light source.

10. The apparatus according to claim 9, wherein said broad-band light source is a halogen lamp.

11. The apparatus according to claim 8, further comprising at least one filter positioned between said at least one luminous source and said detector of said at least one optical web tear detection device.

12. The apparatus according to claim 11, wherein said filter is configured for one of setting and limiting said wavelength range from 200 to 1,100 nm.

13. The apparatus according to claim 11, wherein said detector is configured for measuring in said full wave length range and thereby making a measurement, at least one of said detector and said filter configured for limiting said wave length range for said measurement.

14. The apparatus according to claim 8, wherein said cut-off apparatus is configured for being one of directly and indirectly activated by said at least one optical web tear detection device in accordance with at least one trigger threshold value which has been set.

* * * * *